(12) United States Patent
Sada

(10) Patent No.: US 9,775,352 B2
(45) Date of Patent: Oct. 3, 2017

(54) METHOD OF CONTROLLING PEST

(71) Applicant: SUMITOMO CHEMICAL COMPANY, LIMITED, Tokyo (JP)

(72) Inventor: Yoshinao Sada, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/627,781

(22) Filed: Feb. 20, 2015

(65) Prior Publication Data

US 2015/0157020 A1    Jun. 11, 2015

Related U.S. Application Data

(62) Division of application No. 13/685,936, filed on Nov. 27, 2012, now Pat. No. 8,993,481.

(30) Foreign Application Priority Data

Dec. 8, 2011    (JP) .................. 2011-268615

(51) Int. Cl.
| | | |
|---|---|---|
| *A01N 25/00* | (2006.01) | |
| *A01N 43/653* | (2006.01) | |
| *A01N 43/84* | (2006.01) | |
| *A01N 43/54* | (2006.01) | |
| *A01N 41/06* | (2006.01) | |
| *A01N 33/22* | (2006.01) | |
| *A01N 43/56* | (2006.01) | |
| *A01N 43/32* | (2006.01) | |
| *A01N 33/18* | (2006.01) | |
| *A01N 41/02* | (2006.01) | |

(52) U.S. Cl.
CPC ............. *A01N 43/84* (2013.01); *A01N 33/18* (2013.01); *A01N 33/22* (2013.01); *A01N 41/02* (2013.01); *A01N 41/06* (2013.01); *A01N 43/32* (2013.01); *A01N 43/54* (2013.01); *A01N 43/56* (2013.01); *A01N 43/653* (2013.01)

(58) Field of Classification Search
None
See application file for complete search history.

(56) References Cited

U.S. PATENT DOCUMENTS

| | | | |
|---|---|---|---|
| 7,939,721 B2 | 5/2011 | Arnevik et al. | |
| 2010/0317520 A1 | 12/2010 | Ikeda et al. | |
| 2010/0317523 A1 | 12/2010 | Ikeda et al. | |
| 2011/0009267 A1 | 1/2011 | Suty-Heinze | |
| 2014/0039027 A1* | 2/2014 | Gortz .................. A01N 43/56 514/406 |

FOREIGN PATENT DOCUMENTS

| | | |
|---|---|---|
| EP | 2100506 A2 | 9/2009 |
| WO | WO 02/066471 A | 8/2002 |
| WO | WO 03/030642 A1 | 4/2003 |
| WO | WO 2011/069890 A2 | 6/2011 |
| WO | WO 2011/078400 A1 | 6/2011 |

OTHER PUBLICATIONS

"Growing The Global Food Supply", MeisterPro Crop Protection Handbook, vol. 96, 2010, pp. 7, 373, 563, 582, 496, 383, 384, 200, 201, 222, 374, 380, 381 and 504 (15 pgs.).
Australian Office Action dated Oct. 22, 2015, for Australian Application No. 2012258417.
Examination Report No. 1 issued in the corresponding Australian Patent Application No. 2016210616 dated Jan. 20, 2017.

* cited by examiner

*Primary Examiner* — Alton Pryor
(74) *Attorney, Agent, or Firm* — Birch, Stewart, Kolasch & Birch, LLP

(57) ABSTRACT

Provided is a method which exerts an excellent effect in controlling a pest in a field of soybean, corn or cotton, using a SDHI compound and a PPO-inhibiting compound. A method of controlling a pest (a weed and/or a plant pathogen) in a field of soybean, corn or a cotton, including treating a field before, at or after seeding with a seed of soybean, corn or cotton treated with one or more compounds selected from the group consisting of SDHI compounds, with one or more PPO-inhibiting compounds selected from the group consisting of flumioxazin, sulfentrazone, saflufenacil, oxyfluorfen, fomesafen and a compound of the formula:

5 Claims, No Drawings

METHOD OF CONTROLLING PEST

CROSS-REFERENCE TO RELATED APPLICATIONS

This application is a Divisional of co-pending application Ser. No. 13/685,936 filed on Nov. 27, 2012, which claims priority under 35 U.S.C. §119(a) to Patent Application No. 2011-268615 filed in Japan on Dec. 8, 2011. All of the above applications are hereby expressly incorporated by reference into the present application.

BACKGROUND OF THE INVENTION

Field of the Invention

The present invention relates to a method of controlling a pest, namely, a plant pathogen and a weed.

Description of the Related Art

SDHI compounds have been known as active ingredients of fungicides. PPO-inhibiting compounds have been known as active ingredients of herbicides.

PRIOR ART LITERATURE

Patent Literature

Patent Literature 1: WO 02/066471

Non-Patent Literatures

Non-Patent Literature 1: Crop Protection Handbook, vol. 96 (2010)
Non-Patent Literature 2: Compendium of Pesticide Common Names (http://www.alanwood.net/pesticides/)

SUMMARY OF THE INVENTION

The present invention provides a method which exerts excellent effects in controlling a pest in a field of soybean, corn or cotton.

The present invention relates to the followings.

[1] A method of controlling a weed in a field of soybean, corn or cotton, comprising applying one or more PPO-inhibiting compounds selected from the group consisting of flumioxazin, sulfentrazone, saflufenacil, oxyfluorfen, fomesafen and a compound of the formula:

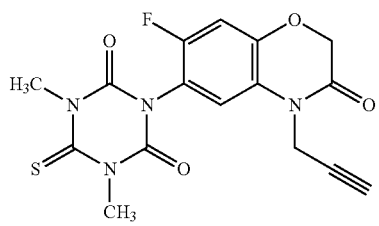

to a field before, at or after seeding with seeds of soybean, corn or cotton treated with one or more compounds selected from the group consisting of SDHI compounds.

[2] A method of controlling a pest in a field of soybean, corn or cotton, comprising steps of:
treating a seed of soybean, corn or cotton with one of more SDHI compounds, and
treating a field before, at or after seeding with the soybean seed, the corn seed or the cotton seed treated with the SDHI compound, with one or more PPO-inhibiting compounds selected from the group consisting of flumioxazin, sulfentrazone, saflufenacil, oxyfluorfen, fomesafen and a compound of the formula:

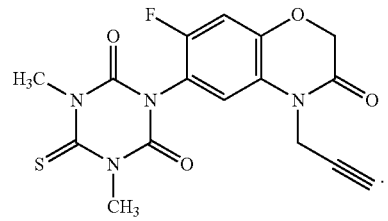

[3] The method of controlling a pest according to [1] or [2], wherein the SDHI compound is selected from the group consisting of sedaxane, penflufen, carboxin, boscalid, furametpyr, flutolanil, fluxapyroxad, isopyrazam, fluopyram and thifluzamide.

[4] The method of controlling a pest according to [1] or [2], wherein the SDHI compound is sedaxane, penflufen or carboxin.

[5] The method of controlling a pest according to [4], wherein the PPO-inhibiting compound is flumioxazin.

[6] The method of controlling a pest according to [2], comprising a step of treating the field before seeding with the seed of soybean, corn or cotton, with the PPO-inhibiting compound.

[7] The method of controlling a pest according to [2], comprising a step of treating the field to be seeded, with the PPO-inhibiting compound simultaneously at seeding with the seed of soybean, corn or cotton.

[8] The method of controlling a pest according to [2], comprising a step of treating the field after seeding with the seed of soybean, corn or cotton, with the PPO-inhibiting compound.

[9] The method of controlling a pest according to [2], wherein the pest is a weed and/or a plant pathogen.

[10] The method of controlling a pest according to [2], wherein the pest is a weed.

DETAILED DESCRIPTION OF THE PREFERRED EMBODIMENTS

The method of controlling a pest according to the present invention includes steps of:
(1) treating a seed of soybean, corn or cotton with one or more SDHI compounds, and
(2) treating a field before, at or after seeding with a seed of soybean, corn or cotton treated with one or more SDHI compounds, with one or more PPO-inhibiting compounds selected from the group consisting of flumioxazin, sulfentrazone, saflufenacil, oxyfluorfen, fomesafen and a compound of the formula:

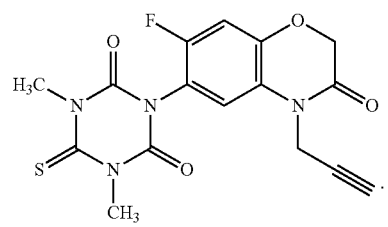 [SMILES: C#CCN1C(=O)COc2cc(F)c(-n3c(=O)n(C)c(=S)n(C)c3=O)cc21]

In the present invention, the seed of soybean, corn or cotton is not limited as far as it is a variety which is generally cultivated as a crop.

Examples of a plant of such a variety include plants to which resistance to a PPO-inhibiting compound such as flumioxazin; a 4-hydroxyphenylpyruvate dioxygenase—inhibiting compound such as isoxaflutole; an acetolactate synthase (hereinafter abbreviated as ALS)—inhibiting compound such as imazethapyr or thifensulfuron methyl; a 5-enolpyruvylshikimate-3-phosphate synthase—inhibiting compound such as glyphosate; a glutamine synthase—inhibiting compound such as glufosinate; and auxin-type herbicide such as 2,4-D or dicamba; or bromoxynil has been imparted by a classical breeding method or a genetic engineering technique.

Examples of a crop to which resistance has been imparted by a classical breeding method include corn resistant to an imidazolinone type ALS—inhibiting herbicide such as imazethapyr, and this has already been commercially available under a trade name of Clearfield (registered trademark). Examples of such a crop also include STS soybean which is resistant to a sulfonylurea—type ALS—inhibiting herbicide such as thifensulfuron methyl. Similarly, examples of a plant to which resistance to an acetyl CoA carboxylase—inhibiting compound such as trione oxime-type or aryloxyphenoxypropionic acid—type herbicide has been imparted by a classical breeding method include SR corn.

Examples of a plant to which resistance has been imparted by a genetic engineering technique include corn, soybean and cotton varieties which are resistant to glyphosate, and they have already been commercially available under trade names of RoundupReady (registered trade mark), Agrisure (registered trademark) GT, Gly-Tol (registered trademark) and the like. Similarly, there are corn, soybean and cotton varieties which are resistant to glufosinate by a genetic engineering technique, and they have already been commercially available under trade names of LibertyLink (registered trademark) and the like. There are corn and soybean varieties under the trade name of Optimum (registered trademark) GAT (registered trade mark), which are resistant to both of glyphosate and an ALS—inhibiting compound. Similarly, there are soybean varieties which are resistant to an imidazolinone—type ALS—inhibiting compound by a genetic engineering technique, and they have been developed under the name of Cultivance. Similarly, there is cotton varieties which are resistant to bromoxynil by a genetic engineering technique, and this has already been commercially available under the trade name of BXN (registered trademark).

A crop such as a soybean which is resistant to dicamba can be produced by introducing a dicamba degrading enzyme such as dicamba monooxygenase isolated from *Pseudomonas maltophilia* into a plant (Behrens et al. 2007 Science 316: 1185-1188).

By introducing a gene encoding aryloxyalkanoate dioxygenase, a crop which becomes resistant to a phenoxy acid-type herbicide such as 2,4-D, MCPA, dichlorprop or mecoprop, and an aryloxyphenoxypropionic acid-type herbicide such as quizalofop, haloxyfop, fluazifop, diclofop, fenoxaprop, metamifop, cyhalofop and clodinafop can be produced (Wright et al. 2010: Proceedings of National Academy of Science. 107 (47): 20240-20245).

The crop includes, for example, a crop which has become possible to synthesize a selective toxin known in *Bacillus* genus, using a genetic engineering technique.

Examples of the toxin which is expressed in such a genetically engineered plant include an insecticidal protein derived from *Bacillus cereus* or *Bacillus popilliae*; a 6-endotoxin such as Cry1Ab, Cry1Ac, Cry1F, Cry1Fa2, Cry2Ab, Cry3A, Cry3Bb1 or Cry9C, derived from *Bacillus thuringiensis*; an insecticidal protein such as VIP1, VIP2, VIP3 or VIP3A; an insecticidal protein derived from nematode; a toxin produced by an animal such as a scorpion toxin, a spider toxin, a bee toxin or an insect-specific neurotoxin; a filamentous fungus toxin; plant lectin; agglutinin; a protease inhibitor such as a trypsin inhibitor, a serine protease inhibitor, patatin, cystatin, and a papain inhibitor; a ribosome inactivating protein (RIP) such as lysine, corn-RIP, abrin, luffin, saporin or bryodin; a steroid metabolism enzyme such as 3-hydroxysteroid oxidase, ecdysteroid-UDP-glycosyltransferase, and cholesterol oxidase; an ecdysone inhibitor; HMG-CoA reductase; an ion channel inhibitor such as a sodium channel inhibitor or a calcium channel inhibitor; juvenile hormone esterase; a diuretic hormone receptor; stilbene synthase; bibenzyl synthase; chitinase; glucanase; and the like.

A toxin expressed by such a genetically engineered crop includes a hybrid toxin of a 8-endotoxin protein such as Cry1Ab, Cry1Ac, Cry1F, Cry1Fa2, Cry2Ab, Cry3A, Cry3Bb1, Cry9C, Cry34Ab or Cry35Ab, and an insecticidal protein such as VIP1, VIP2, VIP3 or VIP3A, and a partially deleted toxin, and a modified toxin. The hybrid toxin can be produced by a new combination of different domains of these proteins using a genetic engineering technique. As the partially deleted toxin, Cry1Ab in which a part of an amino acid sequence has been deleted is known. In the modified toxin, one or a plurality of amino acids of a natural toxin are substituted. Examples of these toxins and recombinant plants which can synthesize these toxins are described in EP-A-0374753, WO 93/07278, WO 95/34656, EP-A-0427529, EP-A-451878, WO 03/052073 and the like. The toxins contained in these recombinant plans impart resistance to Coleoptera vermin, Diptera vermin and Lepidoptera vermin to a plant.

In addition, a genetically engineered plant containing one or a plurality of insecticidal vermin-resistant genes and expressing one or a plurality of toxins has already been known, and some of them are commercially available. Examples of these genetically engineered plants include YieldGard (registered trademark) (corn variety expressing Cry1Ab toxin), YieldGard Rootworm (registered trademark) (corn variety expressing Cry3Bb1 toxin), YieldGard Plus (registered trademark) (corn variety expressing Cry1Ab and Cry3Bb1 toxins), Herculex I (registered trademark) (corn variety expressing phosphinothricin N-acetyltransferase (PAT) for imparting resistance to a Cry1Fa2 toxin and glufosinate), NatureGard (registered trademark), AGRISURE (registered trademark) CB Advantage (Btl1 corn borer (CB) trait), and Protecta (registered trademark).

In addition, genetically engineered cotton containing one or a plurality of insecticidal vermin-resistant genes and expressing one or a plurality of toxins have already been known, and some of them are commercially available. Examples of these genetically engineered cotton include BollGard (registered trademark) (cotton variety expressing Cry1Ac toxin), BollGard (registered trademark) II (cotton variety expressing Cry1Ac and Cry2Ab toxins), BollGard (registered trademark) III (cotton variety expressing Cry1Ac, Cry2Ab and VIP3A toxins), VipCot (registered trademark) (cotton variety expressing VIP3A and Cry1Ab toxins), WideStrike (registered trademark) (cotton variety expressing Cry1Ac and Cry1F toxins).

Examples of the plant used in the present invention also include plants to which resistance to an aphid has been imparted, such as soybeans into which a Rag1 (Resistance Aphid Gene 1) gene has been introduced.

The crop also includes a crop to which the ability to produce an anti-pathogenic substance having selective action has been imparted using a genetic engineering technique. As an example of the anti-pathogenic substance, a PR protein and the like are known (PRPs, EP-A-0392225). Such an anti-pathogenic substance and a genetically engineered plant producing the substance are described in EP-A-0392225, WO 95/33818, EP-A-0353191 and the like. Examples of the anti-pathogenic substance expressed in such a genetically engineered plant include an ion channel inhibitor such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and an anti-pathogenic substance generated by microorganisms, such as a peptide antibiotic, an antibiotic having a hetero ring, or a protein factor associated with resistance to plant diseases (which is called a plant disease-resistant gene and is described in WO 03/000906).

The crop also includes a plant to which a useful character such as oil cake component modification or an amino acid content enhancing character has been imparted using a genetic engineering technique. Examples thereof include VISTIVE (registered trademark) (low linolenic soybean having a reduced linolenic content) and high-lysine (high-oil) corn (corn having an increased lysine or oil content).

Further, stack varieties are also included in which a plurality of the classical herbicide character or herbicide-resistant gene, insecticidal vermin-resistant gene, anti-pathogenic substance production gene, and a useful character such as oil cake component modification or amino acid content enhancing character are combined.

The SDHI compound is also called a Complex II-inhibiting compound, and is a compound exhibiting a series of disease controlling activities, which acts on the mitochondrial electron transport system complex II of filamentous fungus to inhibit succinate dehydrogenase, to thereby inhibit respiration. Examples of the SDHI compound include sedaxane, penflufen, carboxin, boscalid, furametpyr, flutolanil, fluxapyroxad, isopyrazam, fluopyram and thifluzamide.

In the present invention, in the step of treating a seed of soybean, corn or cotton with the SDHI compound, the SDHI compound is usually mixed with a solid carrier or a liquid carrier, formulated with optional addition of an auxiliary agent for formulation, such as a surfactant, then used.

The SDHI compound is applied at a dose in a range of usually 0.001 to 40 g, preferably 0.01 to 10 g per 1 kg of the seed. Examples of a method of applying an active ingredient (i.e., SDHI compound) to a seed of a plant include a method of covering a seed with a preparation containing an active ingredient; a method of immersing a seed in a preparation containing an active ingredient; and a method of coating a seed with a carrier containing an active ingredient.

In the present invention, there is a step of treating a field before, at or after seeding with a seed of soybean, corn or cotton treated with the SDHI compound, with one or more PPO-inhibiting compounds.

The PPO-inhibiting compound is a herbicidally active compound which inhibits protoporphyrinogen IX oxidase (EC1.3.3.4) located on a chlorophyll synthesis pathway in a plastid of a plant and, as a result, leads to withering of the plant.

The PPO-inhibiting compound in the present invention is flumioxazin, sulfentrazone, saflufenacil, oxyfluorfen, fomesafen and a compound of the formula:

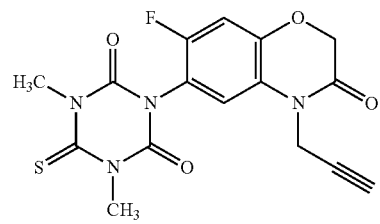 [SMILES: C#CCN1C(=O)COc2cc(F)c(-n3c(=O)n(C)c(=S)n(C)c3=O)cc21]

(hereinafter, may be called compound A). In the present invention, fomesafen includes a free body and sodium salt of fomesafen.

In the step of treating the field with the PPO-inhibiting compound, the PPO-inhibiting compound is usually mixed with a solid carrier or a liquid carrier, formulated with optional addition of an auxiliary agent for formulation, such as a surfactant, and then used.

Examples of a method of treating the field with the PPO-inhibiting compound include a method of applying the PPO inhibitory compound to a soil of the field and a method of applying the PPO-inhibiting compound to a weed after its emergence.

A dose of the PPO-inhibiting compound used in the step of treating a field with the PPO-inhibiting compound is usually in the range of 5 to 5000 g per 10000 m$^2$. In the step of treating a field with the PPO-inhibiting compound, an adjuvant may be mixed upon treatment with the PPO-inhibiting compound.

The seed of soybean, corn or cotton treated with the SDHI compound is seeded on a field by a conventional method. In the method of controlling a pest according to the present invention, the PPO-inhibiting compound may be applied before seeding with the seed of soybean, corn or cotton, may be applied simultaneously at seeding with the seed of soybean, corn or cotton or may be applied after seeding with the seed of soybean, corn or cotton.

When a field is treated with the PPO-inhibiting compound before seeding with the soybean seed or the corn seed, the field is treated with the PPO-inhibiting compound 50 days before seeding to immediately before seeding, preferably 30 days before seeding to immediately before seeding, further preferably 20 days before seeding to immediately before seeding.

When a field is treated with the PPO-inhibiting compound after seeding with the soybean seed or the corn seed, the field is treated with the PPO-inhibiting compound preferably immediately after seeding to 50 days after seeding, more preferably immediately after seeding to 3 days after seeding. Examples of a specific treatment term when a field is treated with the PPO-inhibiting compound after seeding with the soybean seed include a term from preemergence to flowering of the soybean. Among preemergence to flowering of the soybean, preferred is a term from preemergence to 6 compound leaves of the soybean, further preferred is a term from preemergence to 3 compound leaves of the soybean. A specific treating term when a field is treated with the PPO-inhibiting compound after seeding with the corn seed is from preemergence to 12 leaves of the corn, preferably a term from preemergence to 8 leaves of the corn, further preferably a term from preemergence to 6 leaves of the corn. In addition, a leaf age of corn is determined by the Leaf Collar Method.

When a field is treated with the PPO-inhibiting compound before seeding with the cotton seed, the field is treated with the PPO-inhibiting compound 50 days before seeding to immediately before seeding, preferably 30 days before seeding to immediately before seeding, further preferably 20 days before seeding to immediately before seeding.

When a field is treated with the PPO-inhibiting compound after seeding with the cotton seed, the field is treated with the PPO-inhibiting compound immediately after seeding to 70 days after seeding, preferably 30 days after seeding to 50 days after seeding. Examples of a specific treating term when a field is treated with the PPO-inhibiting compound after seeding with the cotton seed include pre-emergence to flowering of the cotton. Preferred is a lignification initiation term of the stem base of the cotton to a term when a lignification portion is 20 cm from the base.

According to the method of controlling a pest of the present invention, a pest such as a plant pathogen and/or a weed in a field of soybean, corn or cotton can be controlled.

Examples of the plant pathogen include the followings:

*Cercospora kikuchii, icrosphaera diffusa, Diaporthe phaseolorum* var. *sojae, Septoria glycines, Cercospora sojina, Phakopsora pachyrhizi, Rhizoctonia solani, Sclerotinia sclerotiorum, Cercospora zeae-maydis, Elsinoe glycines, Ustilago maydis, Cochliobolus heterostrophus, Gloeocercospora sorghi, Cercospora gossypina, Phakopsora gossypii, Colletotrichum gossypii, Peronospora gossypina, Phyotophthora* spp., *Aspergillus* spp., *Penicillium* spp., *Fusarium* spp., *Tricoderma* spp., *Thielaviopsis* spp., *Rhizopus* spp., *Mucor* spp., *Corticium* spp., *Phoma* spp., *Diplodia* spp., *Verticillium* spp., *Puccinia* spp., *Mycosphaerella* spp.

Examples of the weed include the followings:

Urticaceae weeds: *Urtica urens*

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius, Rumex acetosa*

Portulacaceae weeds: *Portulaca oleracea*

Caryophyllaceae weeds: *Stellaria media, Cerastium holosteoides, Cerastium glomeratum, Spergula arvensis, Silene gallica*

Aizoaceae weeds: *Mollugo verticillata*

Chenopodiaceae weeds: *Chenopodium album, Chenopodium ambrosioides, Kochia scoparia, Salsola kali, Atriplex* spp.

Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis, Alternanthera tenella*

Papaveraceae weeds: *Papaver rhoeas, Argemone mexicana*

Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum, Coronopus didymus*

Capparaceae weeds: *Cleome affinis*

Fabaceae weeds: *Aeschynomene indica, Aeschynomene rudis, Sesbania exaltata, Cassia obtusifolia, Cassia occidentalis, Desmodium tortuosum, Desmodium adscendens, Trifolium repens, Pueraria lobata, Vicia angustifolia, Indigofera hirsuta, Indigofera truxillensis, Vigna sinensis*

Oxalidaceae weeds: *Oxalis corniculata, Oxalis strica, Oxalis oxyptera*

Geraniaceae weeds: *Geranium carolinense, Erodium cicutarium*

Euphorbiaceae weeds: *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis, Ricinus communis*

Malvaceae weeds: *Abutilon theophrasti, Sida rhombifolia, Sida cordifolia, Sida spinosa, Sida glaziovii, Sida santaremnensis, Hibiscus trionum, Anoda cristata, Malvastrum coromandelianum*

Sterculiaceae weeds: *Waltheria indica*

Violaceae weeds: *Viola arvensis, Viola tricolor*

Cucurbitaceae weeds: *Sicyos angulatus, Echinocystis lobata, Momordica charantia*

Lythraceae weeds: *Lythrum salicaria*

Apiaceae weeds: *Hydrocotyle sibthorpioides*

Sapindaceae weeds: *Cardiospermum halicacabum*

Primulaceae weeds: *Anagallis arvensis*

Asclepiadaceae weeds: *Asclepias syriaca, Ampelamus albidus*

Rubiaceae weeds: *Galium aparine, Galium spurium* var. *echinospermon, Spermacoce latifolia, Richardia brasiliensis, Borreria alata*

Convolvulaceae weeds: *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides, Jacquemontia tamnifolia*

Boraginaceae weeds: *Myosotis arvensis*

Lamiaceae weeds: *Lamium purpureum, Lamium amplexicaule, Leonotis nepetaefolia, Hyptis suaveolens, Hyptis lophanta, Leonurus sibiricus, Stachys arvensis*

Solanaceae weeds: *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata, Nicandra physaloides*

Scrophulariaceae weeds: *Veronica hederaefolia, Veronica persica, Veronica arvensis*

Plantaginaceae weeds: *Plantago asiatica*

Asteraceae weeds: *Xanthium pensylvanicum, Xanthium occidentale, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza canadensis, Ambrosia artemisiaefolia, Ambrosia trifida, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium*

*perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis*

Liliaceae weeds: *Allium canadense, Allium vineale*

Commelinaceae weeds: *Commelina communis, Commelina bengharensis, Commelina erecta*

Poaceae weeds: *Echinochloa crus-galli, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Alospecurus aequalis, Alopecurus myosuroides, Avena fatua, Sorghum halepense, Sorghum vulgare, Agropyron repens, Lolium multiflorum, Lolium perenne, Lolium rigidum, Bromus secalinus, Bromus tectorum, Hordeum jubatum, Aegilops cylindrica, Phalaris arundinacea, Phalaris minor, Apera spicaventi, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rynchelitrum repens, Dactyloctenium aegyptium, Ischaemum rugosum, Oryza sativa, Paspalum notatum, Paspalum maritimum, Pennisetum clandestinum, Pennisetum setosum, Rottboellia cochinchinensis*

Cyperaceae weeds: *Cyperus microiria, Cyperus iria, Cyperus odoratus, Cyperus rotundus, Cyperus esculentus, Kyllinga gracillima*

Equisetaceae weeds: *Equisetum arvense, Equisetum palustre*, and the like.

In the method of controlling a pest of the present invention, one or more kinds of other agrochemicals can be also used in combination simultaneously or separately with the SDHI compound or the PPO-inhibiting compound. Examples of the other agrochemicals include an insecticide, a miticide, a nematocide, a fungicide, a herbicide, a plant regulating agent and a safener.

Examples of the other agrochemicals include the following:

Herbicide: dicamba and a salt thereof (diglycolamine salt, dimethylammonium salt, isopropylammonium salt, potassium salt, sodium salt, choline salt), 2,4-D and a salt or ester thereof (butotyl ester, dimethylammonium salt, diolamine salt, ethylhexyl ester, isooctyl ester, isopropylammonium salt, sodium salt, triisopropanolamine salt, choline salt), 2,4-DB and a salt or ester thereof (dimethylammonium salt, isooctyl ester, choline salt), MCPA and a salt or ester thereof (dimethylammonium salt, 2-ethylhexyl ester, isooctyl ester, sodium salt, choline salt), MCPB, mecoprop and a salt or ester thereof (dimethylammonium salt, diolamine salt, ethadyl ester, 2-ethylhexyl ester, isooctyl ester, methyl ester, potassium salt, sodium salt, trolamine salt, choline salt), mecoprop-P and a salt or ester thereof (dimethylammonium salt, 2-ethylhexyl ester, isobutyl salt, potassium salt, choline salt), dichlorprop and a salt or ester thereof (butotyl ester, dimethylammonium salt, 2-ethylhexyl ester, isooctyl ester, methyl ester, potassium salt, sodium salt, choline salt), dichlorprop-P, dichlorprop-P-dimethylammonium, bromoxynil, bromoxynil-octanoate, dichlobenil, ioxynil, ioxynil-octanoate, di-allate, butylate, tri-allate, phenmedipham, chlorpropham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, aminocyclopyrachlor-methyl, aminocyclopyrachlor-potassium, trifluralin, pendimethalin, ethalfluralin, benfluralin, prodiamine, simazine, atrazine, propazine, cyanazine, ametryn, simetryn, dimethametryn, prometryn, indaziflam, triaziflam, metribuzin, hexazinone, isoxaben, diflufenican, diuron, linuron, fluometuron, difenoxuron, methyl-daimuron, isoproturon, isouron, tebuthiuron, benzthiazuron, methabenzthiazuron, propanil, mefenacet, clomeprop, naproanilide, bromobutide, daimuron, cumyluron, diflufenzopyr, etobenzanid, bentazon, tridiphane, indanofan, amitrole, fenchlorazole, clomazone, maleic hydrazide, pyridate, chloridazon, norflurazon, bromacil, terbacil, oxaziclomefone, cinmethylin, benfuresate, cafenstrole, pyrithiobac, pyrithiobac-sodium, pyriminobac, pyriminobac-methyl, bispyribac, bispyribac-sodium, pyribenzoxim, pyrimisulfan, pyriftalid, fentrazamide, dimethenamid, dimethenamid-P, ACN, bennzobicyclon, dithiopyr, triclopyr and a salt or ester thereof (butotyl ester, triethylammonium salt), fluroxypyr, fluroxypyr-meptyl, thiazopyr, aminopyralid and a salt thereof (potassium salt, triisopropanolammonium salt, choline salt), clopyralid and a salt thereof (olamine salt, potassium salt, triethylammonium salt, choline salt), picloram and a salt thereof (potassium salt, triisopropanolammonium salt, choline salt), dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium, trifloxysulfuron, chlorsulfuron, cinosulfuron, ethametsulfuron, ethametsulfuron-methyl, iodosulfuron, iodosulfuron-methyl-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, mesotrione, sulcotrione, tefuryltrione, tembotrione, isoxachlortole, isoxaflutole, benzofenap, pyrasulfotole, pyrazolynate, pyrazoxyfen, topramezone, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazapyr-ammonium, imazaquin, imazaquin-ammonium, imazethapyr, imazethapyr-ammonium, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, pyroxasulfone, glyphosate, glyphosate-isopropylamine, glyphosate-trimethylsulfonium, glyphosate-ammonium, glyphosate-diammonium, glyphosate-sodium, glyphosate-potassium, glyphosate-guanidine, glufosinate, glufosinate-ammonium, glufosinate-P, glufosinate-P-sodium, bialafos, anilofos, bensulide, butamifos, paraquat, paraquat-dichloride, diquat anddiquat-dibromide Plant growth regulating agents: hymexazol, paclobutrazol, uniconazole, uniconazole-P, inabenfide, prohexadione-calcium, 1-methylcyclopropene, trinexapac and gibberellins.

Safeners: benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride and oxabetrinil.

EXAMPLES

The present invention will be described below by way of examples, but the present invention is not limited to these examples.

First, evaluation criteria of herbicidal activity and phytotoxicity on crop will be shown.

Evaluation of herbicidal activity is classified into 0 to 100, letting no or little difference when the state of germination or growth of a test weed at investigation is compared with that of non-treatment to be "0", and letting complete withering of a test weed or complete inhibition of germination or growth to be "100".

For evaluation of phytotoxicity on crop, when phytotoxicity is hardly perceived, it is represented by "no damage", when slight phytotoxicity is perceived, it is represented by "slight", when moderate phytotoxicity is perceived, it is represented by "moderate", and when severe phytotoxicity is perceived, it is represented by "severe".

Example 1

Pre-Plant Application in Cotton

In combinations shown in Table 1, herbicidal activity against a weed and phytotoxicity on a crop can be confirmed according to the aforementioned criteria, by the following method.

A soil is packed into a pot, a weed is seeded, and the soil surface is uniformly treated with a PPO-inhibiting compound. After 15 days, cotton seeds with a SDHI compound attached thereto are seeded. This pot is placed in a greenhouse. Fifteen days after seeding, the herbicidal activity against the weed is investigated.

TABLE 1

| Combination | SDHI compound | PPO-inhibiting compound |
|---|---|---|
| 1-1 | Sedaxane | Flumioxazin |
| 1-2 | Penflufen | Flumioxazin |
| 1-3 | Carboxin | Flumioxazin |
| 1-4 | Sedaxane | Fomesafen |
| 1-5 | Penflufen | Fomesafen |
| 1-6 | Carboxin | Fomesafen |
| 1-7 | Sedaxane | Oxyfluorfen |
| 1-8 | Penflufen | Oxyfluorfen |
| 1-9 | Carboxin | Oxyfluorfen |
| 1-10 | Sedaxane | Saflufenacil |
| 1-11 | Penflufen | Saflufenacil |
| 1-12 | Carboxin | Saflufenacil |
| 1-13 | Sedaxane | Compound A |
| 1-14 | Penflufen | Compound A |
| 1-15 | Carboxin | Compound A |

Example 2

Post-Directed Application in Cotton

In combinations shown in Table 2, herbicidal activity against a weed and phytotoxicity on a crop can be confirmed according to the aforementioned criteria, by the following method.

A SDHI compound is attached to each of cotton seeds. Then, the seeds are seeded on a cultivated land. Thirty days after seeding, in the state where the main stem of cotton is lignified 15 cm from the ground surface, the cultivated land is subjected to Post-directed application with a PPO-inhibiting compound. Twenty eight days after the treatment, the herbicidal activity against the weed is investigated.

TABLE 2

| Combination | SDHI compound | PPO-inhibiting compound |
|---|---|---|
| 2-1 | Sedaxane | Flumioxazin |
| 2-2 | Penflufen | Flumioxazin |
| 2-3 | Carboxin | Flumioxazin |
| 2-4 | Sedaxane | Fomesafen |
| 2-5 | Penflufen | Fomesafen |
| 2-6 | Carboxin | Fomesafen |
| 2-7 | Sedaxane | Oxyfluorfen |
| 2-8 | Penflufen | Oxyfluorfen |
| 2-9 | Carboxin | Oxyfluorfen |
| 2-10 | Sedaxane | Saflufenacil |
| 2-11 | Penflufen | Saflufenacil |
| 2-12 | Carboxin | Saflufenacil |
| 2-13 | Sedaxane | Compound A |
| 2-14 | Penflufen | Compound A |
| 2-15 | Carboxin | Compound A |

Example 3

Pre-Plant Application in Soybean

In combinations shown in Table 3, a controlling effect on a weed and phytotoxicity on a crop can be confirmed according to the aforementioned criteria, by the following method.

A soil is packed into a pot, a weed is seeded, and a soil surface is uniformly treated with a PPO-inhibiting compound. After 7 days, soybean seeds with a SDHI compound attached thereto are seeded. This pot is placed in a greenhouse. Fifteen days after seeding, the herbicidal activity against the weed is investigated.

TABLE 3

| Combination | SDHI compound | PPO-inhibiting compound |
|---|---|---|
| 3-1 | Sedaxane | Flumioxazin |
| 3-2 | Penflufen | Flumioxazin |
| 3-3 | Carboxin | Flumioxazin |
| 3-4 | Sedaxane | Fomesafen |
| 3-5 | Penflufen | Fomesafen |
| 3-6 | Carboxin | Fomesafen |
| 3-7 | Sedaxane | Saflufenacil |
| 3-8 | Penflufen | Saflufenacil |
| 3-9 | Carboxin | Saflufenacil |
| 3-10 | Sedaxane | Oxyfluorfen |
| 3-11 | Penflufen | Oxyfluorfen |
| 3-12 | Carboxin | Oxyfluorfen |
| 3-13 | Sedaxane | Compound A |
| 3-14 | Penflufen | Compound A |
| 3-15 | Carboxin | Compound A |
| 3-16 | Sedaxane | Sulfentrazone |

TABLE 3-continued

| Combination | SDHI compound | PPO-inhibiting compound |
|---|---|---|
| 3-17 | Penflufen | Sulfentrazone |
| 3-18 | Carboxin | Sulfentrazone |

Example 4

Preemergence Application in Soybean

In combinations shown in Table 4, herbicidal activity against a weed and phytotoxicity on a crop can be confirmed according to the aforementioned criteria, by the following method.

A SDHI compound is attached to each of soybean seeds. Then, a soil is packed into a pot, and the seeds and seeds of a weed are seeded. On the day of the seeding, the soil surface is uniformly treated with a PPO-inhibiting compound. This pot is placed in a greenhouse. Fifteen days after seeding, the herbicidal activity against the weed is investigated.

TABLE 4

| Combination | SDHI compound | PPO-inhibiting compound |
|---|---|---|
| 4-1 | Sedaxane | Flumioxazin |
| 4-2 | Penflufen | Flumioxazin |
| 4-3 | Carboxin | Flumioxazin |
| 4-4 | Sedaxane | Fomesafen |
| 4-5 | Penflufen | Fomesafen |
| 4-6 | Carboxin | Fomesafen |
| 4-7 | Sedaxane | Saflufenacil |
| 4-8 | Penflufen | Saflufenacil |
| 4-9 | Carboxin | Saflufenacil |
| 4-10 | Sedaxane | Compound A |
| 4-11 | Penflufen | Compound A |
| 4-12 | Carboxin | Compound A |
| 4-13 | Sedaxane | Sulfentrazone |
| 4-14 | Penflufen | Sulfentrazone |
| 4-15 | Carboxin | Sulfentrazone |

Example 5

Preemergence Application in Corn

In combinations shown in Table 5, herbicidal activity against a weed and phytotoxicity on a crop can be confirmed according to the aforementioned criteria, by the following method.

A SDHI compound is attached to each of corn seeds. Then, a soil is packed into a pot, and the seeds and seeds of a weed are seeded. On the day of the seeding, the soil surface is uniformly treated with a PPO-inhibiting compound. This pot is placed in a greenhouse. Fifteen days after the seeding, the herbicidal activity against the weed is investigated.

TABLE 5

| Combination | SDHI compound | PPO-inhibiting compound |
|---|---|---|
| 5-1 | Sedaxane | Saflufenacil |
| 5-2 | Penflufen | Saflufenacil |
| 5-3 | Carboxin | Saflufenacil |
| 5-4 | Sedaxane | Compound A |
| 5-5 | Penflufen | Compound A |
| 5-6 | Carboxin | Compound A |

Example 6

Pre-Plant Application in Corn

In combinations shown in Table 6, herbicidal activity against a weed and phytotoxicity on a crop can be confirmed according to the aforementioned criteria, by the following method.

A soil is packed in a pot, a weed is seeded, and the soil surface is uniformly treated with a PPO-inhibiting compound. After 7 days, corn seeds with a SDHI compound attached thereto are seeded. This pot is placed in a greenhouse. Fifteen days after the seeding, the herbicidal activity against the weed is investigated.

TABLE 6

| Combination | SDHI compound | PPO-inhibiting compound |
|---|---|---|
| 6-1 | Sedaxane | Flumioxazin |
| 6-2 | Penflufen | Flumioxazin |
| 6-3 | Carboxin | Flumioxazin |
| 6-4 | Sedaxane | Saflufenacil |
| 6-5 | Penflufen | Saflufenacil |
| 6-6 | Carboxin | Saflufenacil |
| 6-7 | Sedaxane | Compound A |
| 6-8 | Penflufen | Compound A |
| 6-9 | Carboxin | Compound A |

According to the method of controlling a pest according to the present invention, a pest in a field of soybean, corn or cotton can be effectively controlled.

What is claimed is:

1. A method of controlling a weed in a field of soybean, comprising applying sulfentrazone to a field before, at or after seeding with a seed of soybean treated with penflufen.

2. A method of controlling a weed in a field of soybean, comprising steps of:
   treating a seed of soybean with penflufen, and
   treating a field before, at or after seeding with the seed of soybean treated with the penflufen, with sulfentrazone.

3. The method of controlling a weed according to claim 2, comprising a step of treating the field before seeding with the seed of soybean with the sulfentrazone.

4. The method of controlling a weed according to claim 2, comprising a step of treating the field to be seeded, with the sulfentrazone simultaneously at seeding with the seed of soybean.

5. The method of controlling a weed according to claim 2, comprising a step of treating the field after seeding with the seed of soybean, with the sulfentrazone.

* * * * *